(12) United States Patent
Shaw

(10) Patent No.: US 8,541,047 B1
(45) Date of Patent: Sep. 24, 2013

(54) POLAR ANTISEPTIC/ANTIBACTERIAL CONTAINING TOOTHPICK PROBES

(76) Inventor: Richard J. Shaw, Pewaukee, WI (US)

( * ) Notice: Subject to any disclaimer, the term of this patent is extended or adjusted under 35 U.S.C. 154(b) by 1062 days.

(21) Appl. No.: 12/077,916

(22) Filed: Mar. 24, 2008

(51) Int. Cl.
*A61C 15/04* (2006.01)
*A01N 25/02* (2006.01)
*A61C 3/00* (2006.01)

(52) U.S. Cl.
USPC ............ 427/2.29; 424/43; 424/400; 424/401; 424/404; 424/435; 433/141

(58) Field of Classification Search
None
See application file for complete search history.

(56) References Cited

U.S. PATENT DOCUMENTS

| | | | | |
|---|---|---|---|---|
| 3,674,901 | A | * | 7/1972 | Shepherd et al. ............. 424/443 |
| 5,002,769 | A | | 3/1991 | Friedman |
| 5,503,842 | A | * | 4/1996 | Fazan et al. .................. 424/443 |
| 5,875,798 | A | | 3/1999 | Petrus |
| 2005/0058609 | A1 | | 3/2005 | Nazeri |
| 2006/0070195 | A1 | * | 4/2006 | Morita et al. .................. 15/105 |
| 2006/0243409 | A1 | * | 11/2006 | Fish et al. ..................... 162/329 |

FOREIGN PATENT DOCUMENTS

| | | | | |
|---|---|---|---|---|
| FR | 2 908 047 | * | 5/2008 | |
| WO | WO 2008/068400 | * | 7/2008 | |

OTHER PUBLICATIONS

Wyzgoski et al.; J. of Materials Science 22 (1987) 1715-1723.*
Perkin-Elmer study: "Nylon 6—Influence of Water on Mechanical Properties and Tg"; web site address: "http://www.perkinelmer.com/CMSResources/Images/44-74182APP_InfluenceofWaterOnMechPropsandTG.pdf"; dated 2007; downloaded 28 No. 2012.*

* cited by examiner

*Primary Examiner* — Robert A Wax
*Assistant Examiner* — Jeffrey T Palenik
(74) *Attorney, Agent, or Firm* — Robert T Johnson

(57) ABSTRACT

A toothpick probe molded of nylon 6 material and containing absorbed polar mouthwash antiseptic/antibacterial solution for probing between human teeth and probing of the gums holding the human teeth. The toothpick probe molded of nylon 6 material is captured immediately on ejection from the molding cavities and immersed in a polar antiseptic mouthwash solution and subsequently removed from the solution and free liquid removed from the toothpick probes for subsequent use of the toothpick probes, as a toothpick probe for human teeth and gums holding the teeth and in addition a molded nylon 6 material is captured and immersed in a polar solution of antiseptic/antibacterial for a sufficient time to absorb at least 10% of its weight of the antiseptic/antibacterial solution and a section of the molded nylon 6 material containing the absorbed polar antiseptic/antibacterial liquid, for in vivo application.

Figure 1:
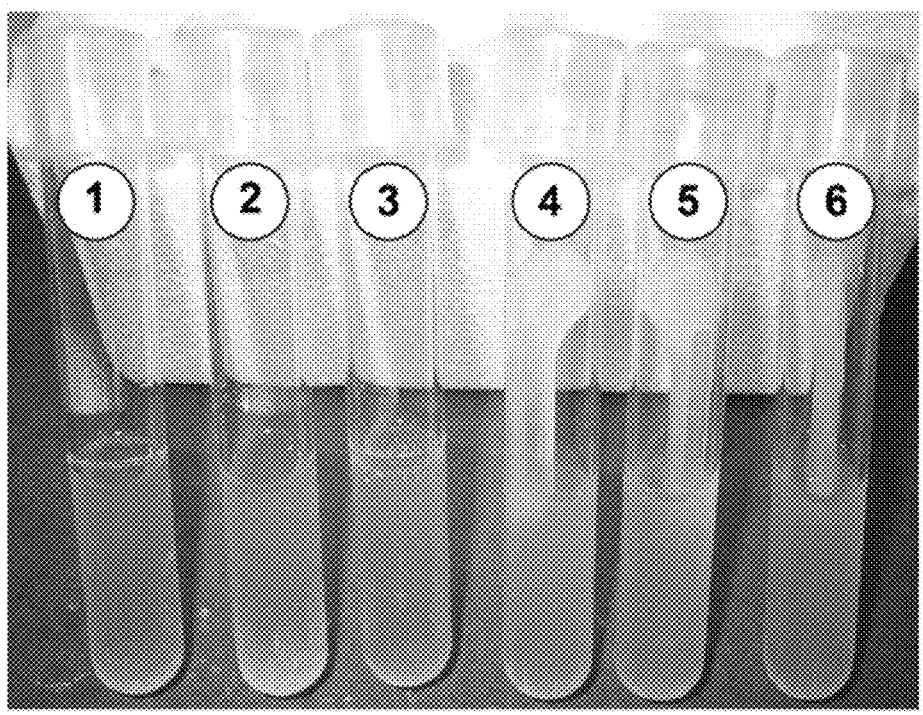

2 Claims, 6 Drawing Sheets
(6 of 6 Drawing Sheet(s) Filed in Color)

POLAR ANTISEPTIC/ANTIBACTERIAL CONTAINING TOOTHPICK PROBES

BACKGROUND OF THE INVENTION

Using a conventional toothpick for picking between the human teeth is fraught with danger due to possible irritation of the gum line, and even introducing new bacteria into the human mouth.

SUMMARY OF THE INVENTION

To avoid introduction of new bacteria into the human mouth, the antiseptic/antibacterial toothpick probes of this invention is a polar liquid absorbing plastic molding of nylon 6 material to absorb polar liquid antiseptic/antibacterial compounds penetrating the toothpick probe, and the antiseptic/antibacterial compound is leached out of the antiseptic/antibacterial toothpick probes, in vivo, by saliva, in contact with the antiseptic/antibacterial laden toothpick used as a probe.

PRIOR ART REFERENCES

U.S. Pat. No. 5,875,798 for THERAPEUTIC TOOTHPICK
U.S. Pat. No. 5,002,769 for COMPOSITION FOR—RELEASE OF CHLORHEXIDINE
Pub. No. US 2005/0058609 A1 for MEDICATED TOOTHPICK.

None of the above prior art references would anticipate this present invention, or collectively make obvious this present invention.

An object of this invention is to disclose a toothpick probe, formed or molded of nylon 6 material and containing therein absorbed polar liquid antiseptic/antibacterial compounds.

Another object of this invention is to disclose a toothpick probe formed of nylon 6 material and containing absorbed polar liquid antiseptic/antibacterial compounds and applying the toothpick probe, containing the antiseptic/antibacterial compounds in vivo, to a human mouth and the antiseptic/antibacterial compound is leached from the antiseptic/antibacterial containing toothpick probe on manipulation of the toothpick between the teeth and gums of the human mouth.

Another object of this invention is to disclose an in vivo procedure of molded nylon 6 material having absorbed therein, by immersion, in a polar solution of antiseptic/antibacterial components for a time sufficient to absorb at least 18% of the weight of nylon 6 molding, and the molded nylon 6 tooth and gum probe containing the antiseptic/antibacterial, used in vivo, as a probe on the teeth and gums.

In the following discussion the term "antiseptic" is also meant to include "antibacterial". (e.g. antiseptic/antibacterial) EQUATE® WALMART CO. BENTONVILLE, ARK.
Protocol for Testing of Antiseptic Toothpick Also Identified as RXPIX.

The procedure for testing and findings are shown in the following pages 3 and 4.
Pprotocol For Testing of Antimicrobial RXPIX
1. Overview For each sample three replicate experiments were performed. Briefly, a drop of the bacterium *E. Coli* (strain DH5a) was mixed with a small amount of medium (Loria-Bertani Broth, or LB Broth and allowed to exchange fluid with the RXPIX for 15 minutes. After this period of time, 2 ml of LB Broth were added to each tube and the bacteria were allowed to grow for 20 hours at 37° C. Observing the turbidity of the broth at this time assessed bacterial viability. Bacterial viability was also assessed analytically by measuring the absorbance of visible light (600 nm)

11. Procedure

A. On day 1, a frozen stock of DH5a was thawed and used to inoculate 5 ml of LB Broth The LB broth was incubated at 37° C. for 24 hours and bacterial growth was observed as an increase in turbidity. A small amount (~50 microliter) of bacterial medium was removed for use in this experiment.

B. On Day 2, 1 micro liter of E. Coli cells was transferred to each 12×75 nim round-bottom tube for antimicrobial testing. In addition 5 microliters of fresh LB Broth were added to each tube to allow for fluid exchange. Finally, the RXPIX were removed from their respective fluid-filled containers, dried to remove excess fluid, and inserted into the round-bottom tubes tip first to allow for fluid exchange between the medium, the bacteria, and the tip of the RXPIX. The tubes were then agitated at room temperature for 15 minutes to ensure adequate fluid exchange and to allow the antimicrobial to take effect.

C. After 15 minutes of agitation, 2 ml of LB Broth was added to each round-bottom tube. The tubes were then transferred to a 37° C. incubator and shaken at 275 cycles/minute for a period of 20 hours.

D. After 20 hours of incubation, bacterial viability was assessed

Visually turbidity of the LB broth indicated bacterial growth (and therefore negligible antimicrobial activity). Clarity of the LB broth indicated the absence of bacterial growth and therefore robust antibacterial activity.

E. To further characterize bacterial growth, the absorbance of 600 nm visible light was used to analytically measure turbidity. The broth from each sample was measured with a spectrophotometer equipped with a lamp emitting visible light.

111. Results

Bacterial growth occurred in tubes that were exposed to unsoaked RXPIX. Bacterial growth also occurred in tubes that were exposed to only water (positive control) No bacterial growth occurred in tubes that were incubated with treated RXPIX. Further more, no bacterial growth occurred in tubes that were incubated with 70% ethanol (negative control). Detailed results (both digital pictures and spectrophotonetric readings) are attached.

IV. Conclusions

The RXPIX are bactericidal and exhibit potent and specific antimicrobial activity.

BRIEF DESCRIPTION OF COLOR TEST SETS DISCLOSED AND SHOWN

The patent or application file contains at least one drawing executed in color. Copies of this patent or patent application publication with color drawing(s) will be provided by the Office upon request and payment of the necessary fee.

FIG. 1—Triple test showing of inoculated broth vials 1, 2, 3, 4, 5, 6. This is a negative control showing all vials of broth and each vial inoculated with bacteria and in vials 1, 2, 3 there is shown a toothpick probe with no antiseptic material contained on the toothpick probe. The turbidity "bacterial growth" shows in inoculated broth in vials 1, 2, 3, 4, 5, and 6 but omitting antiseptic containing toothpick probes of this invention.

Figure 2:
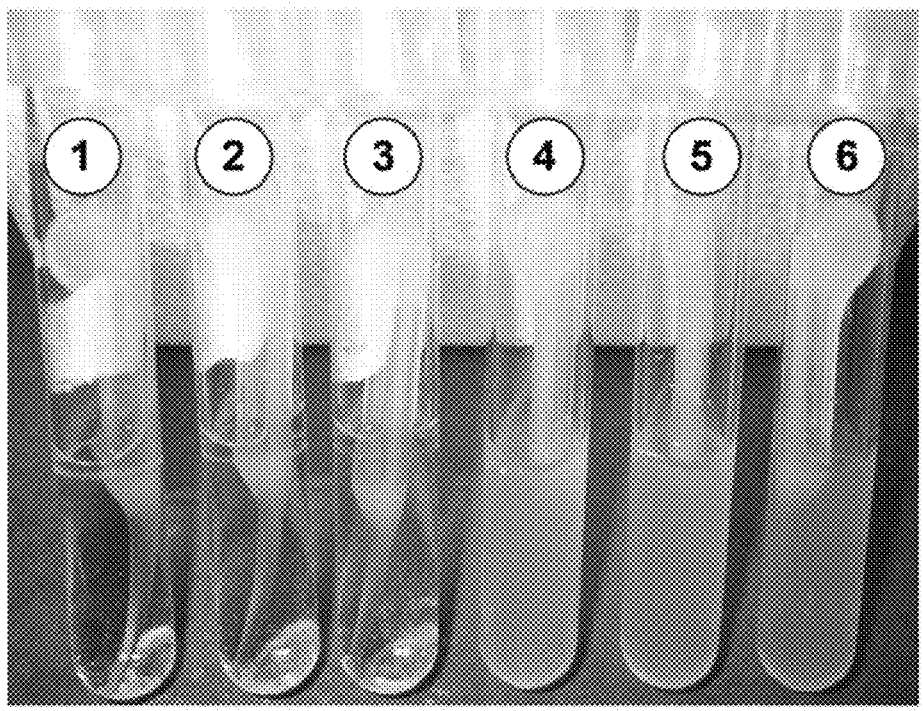

FIG. 2—Triple test showing sterility "no turbidity" of inoculated broth vials plus antiseptic toothpick probe 1, 2, 3 and turbidity of inoculated broth in vials 4, 5, 6 but without antiseptic containing toothpick probes. Antiseptic of Mint mouthwash contained on toothpick probe.

Figure 3:
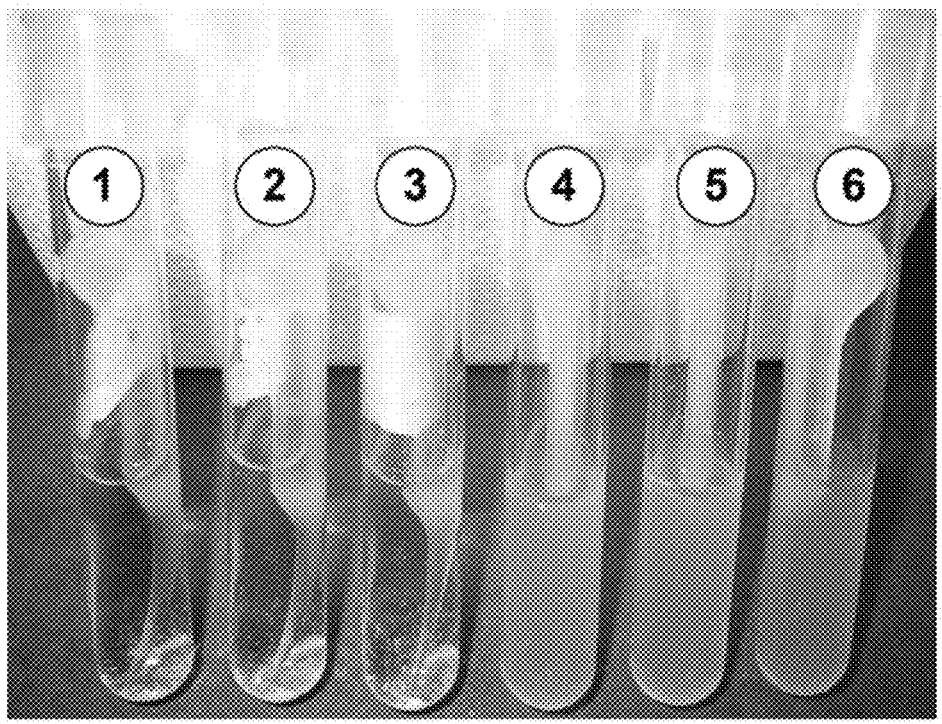

FIG. 3—This is a duplicate test of FIG. 2.

Figure 4:
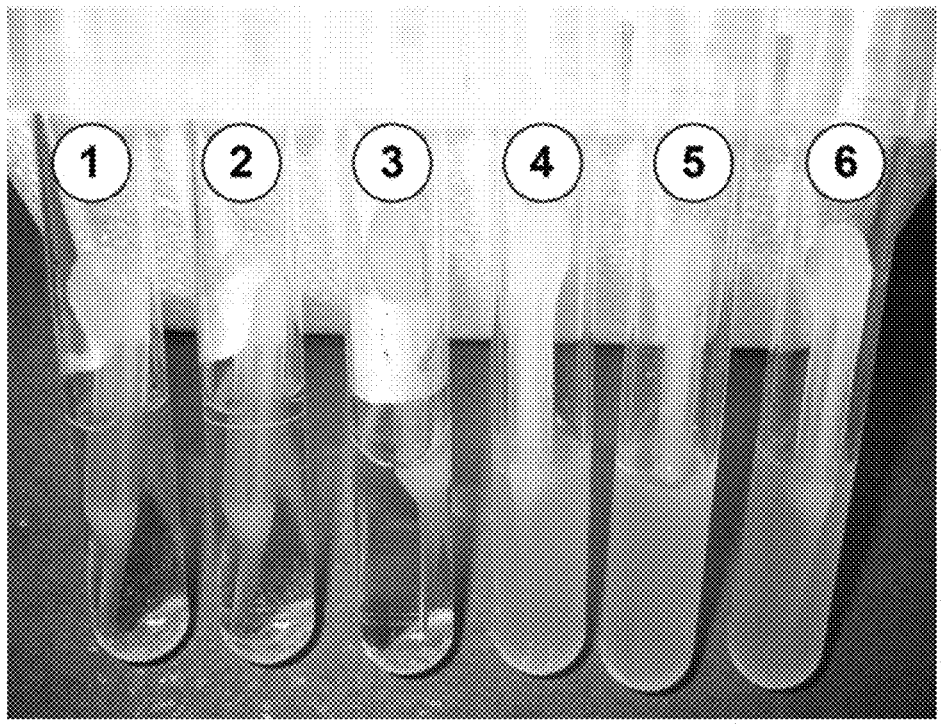

FIG. 4—This is a duplicate test of FIG. 2, but with CITRUS mouth wash.

Figure 5:
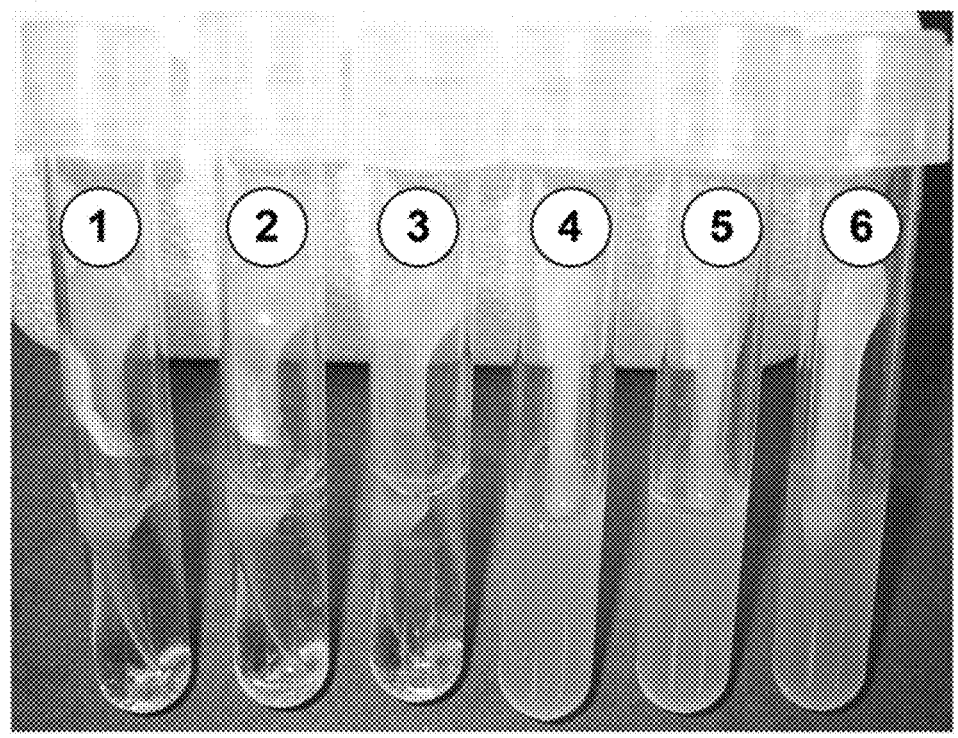

FIG. 5—This is a duplicate test of FIG. 4, with MINT mouth wash.

Figure 6:
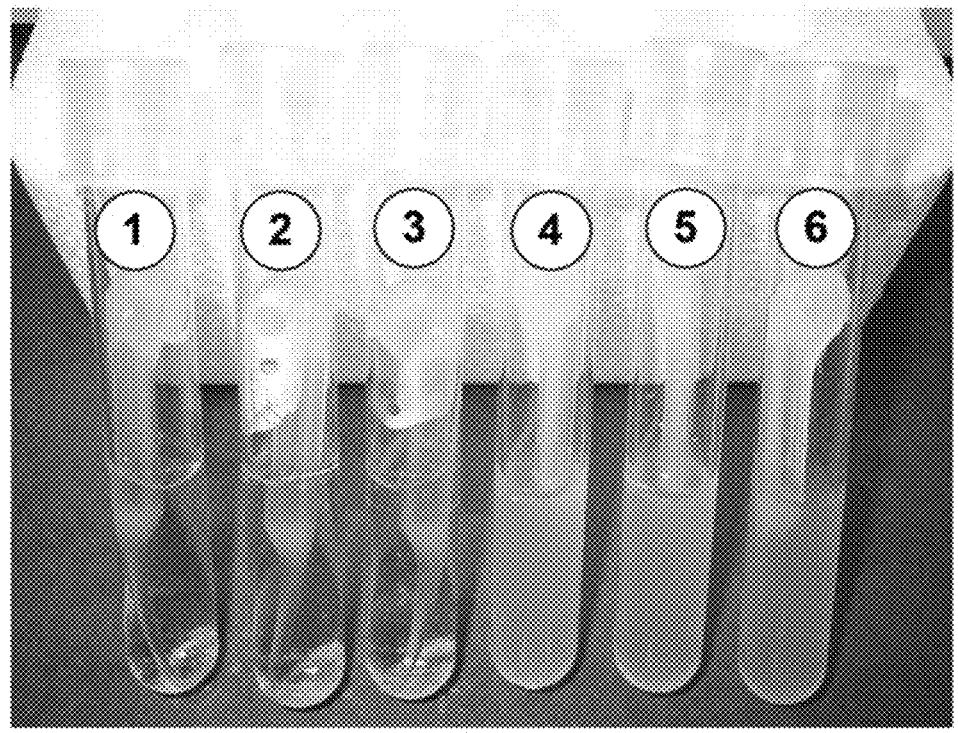

FIG. 6—This is a duplicate procedure of FIG. 5 with CITRUS mouth wash plus 0.5% sanguinaria contained on the tooth pick probe placed in vials 1, 2, 3.

Figure 7:
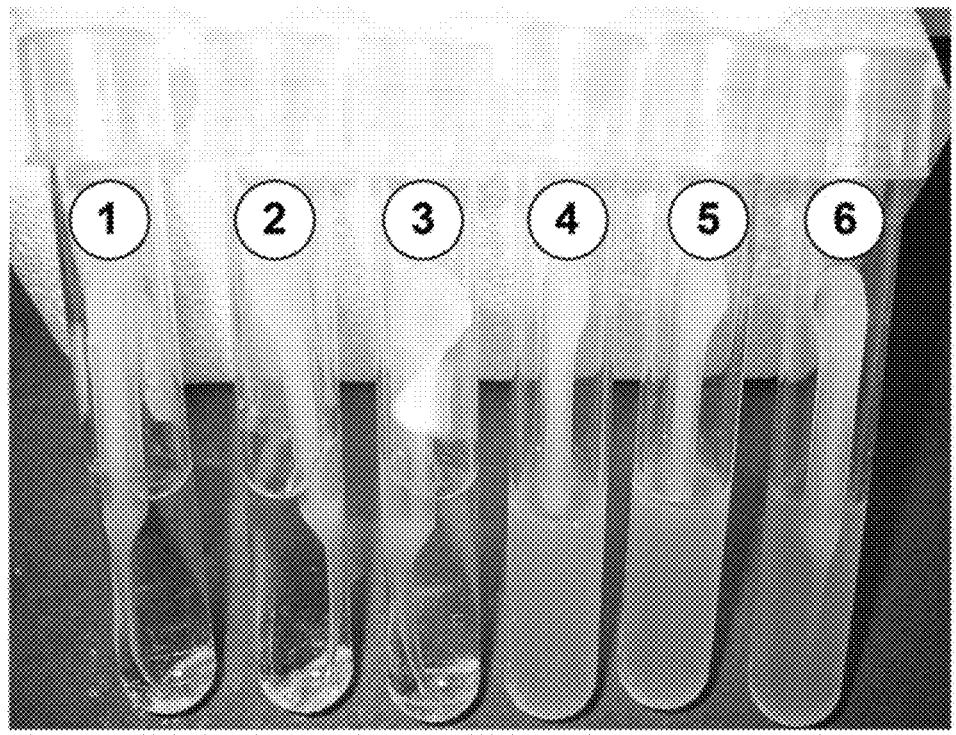

FIG. 7—Toothpick probes immersed in 90% ethyl alcohol, air dried and toothpick probes added to vials 1, 2, 3.

Figure 8:
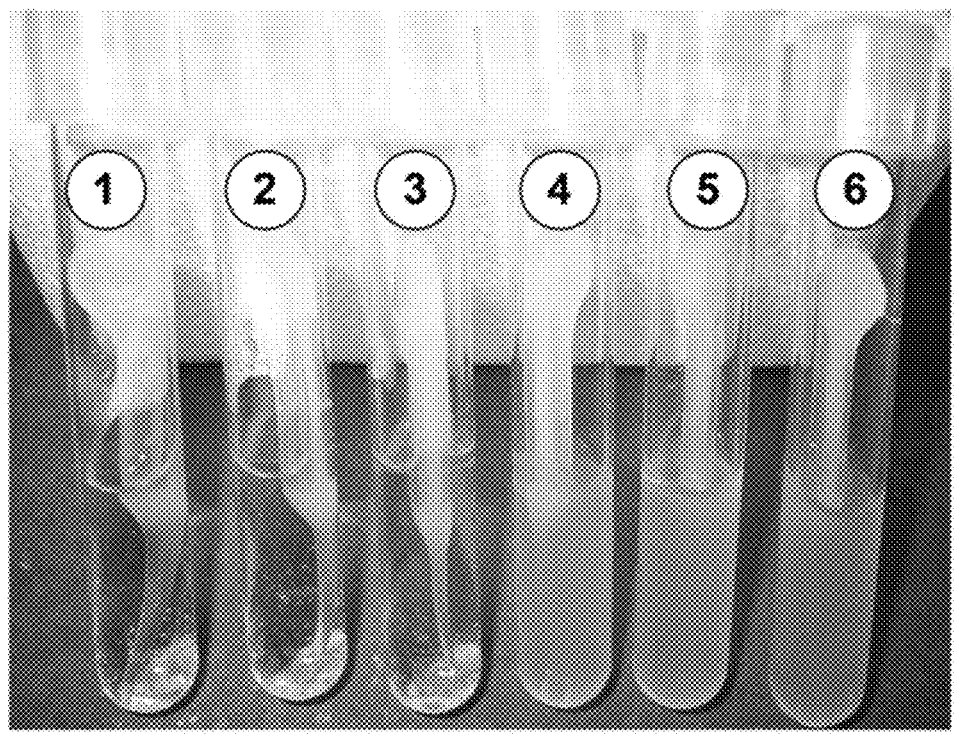

FIG. 8—This is a duplicate procedure of FIG. 7.

Figure 9:
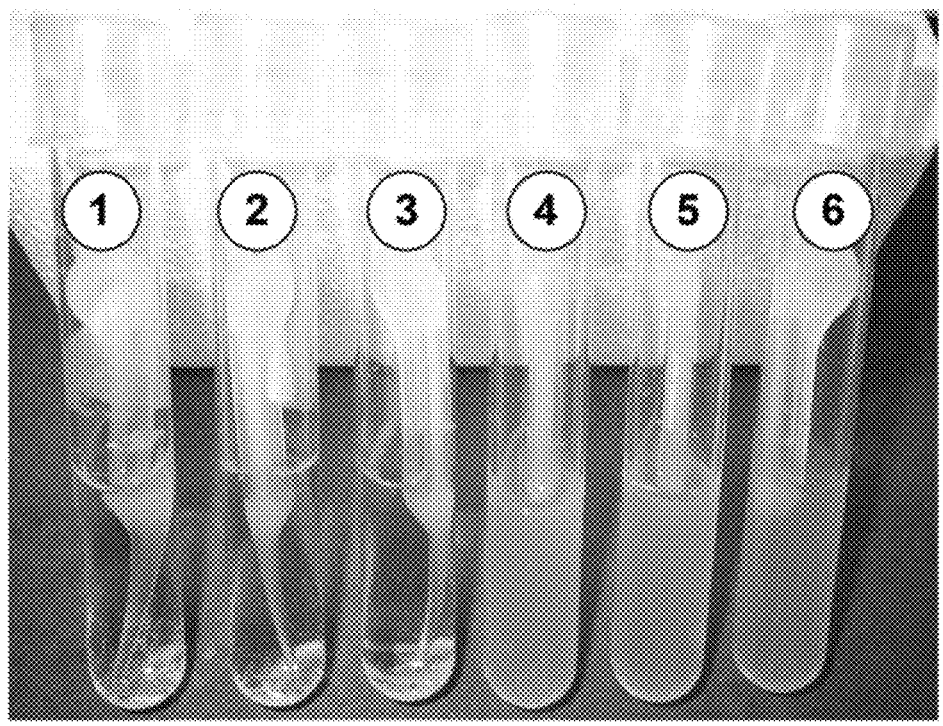

FIG. 9—Toothpick probes immersed in 90% ethyl alcohol, air dried, plus 0.5% sanguinaria, added to vials 1, 2, 3

Figure 10:
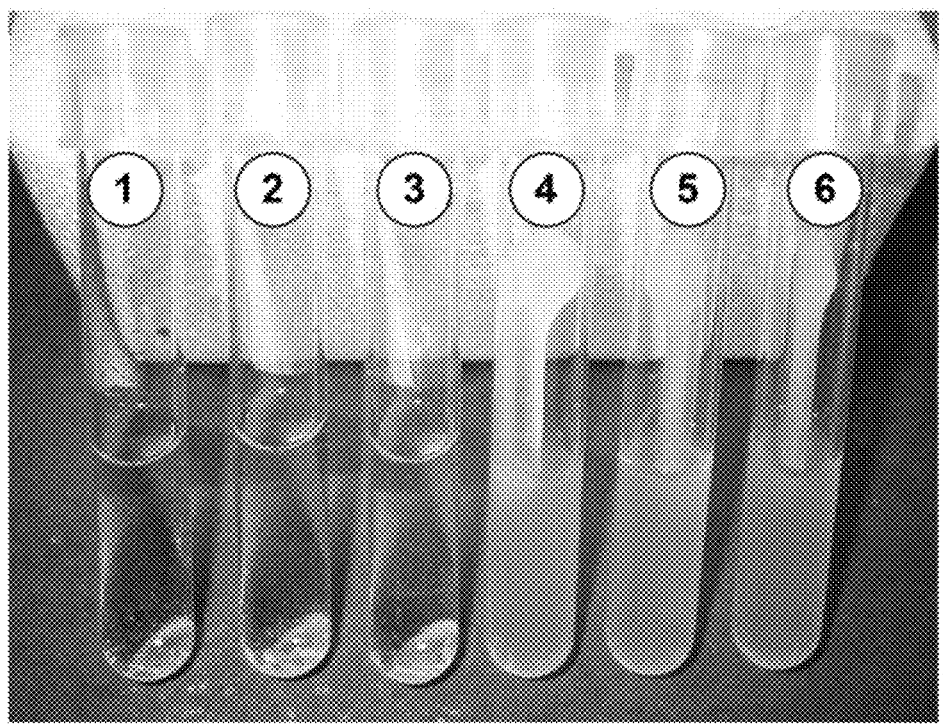

FIG. 10—200 microliters of 70% Ethyl alcohol added to each inoculated vial 1, 2, and 3 as a negative control. (not showing bacterial growth) but bacterial growth shown by turbidity of vials 4, 5, 6.) All sets from FIG. 1 through FIG. 10 shows the efficacy of toothpick probe (a.k.a.) RXPIX containing antiseptic/antibacterial shows prevention of bacterial growth, in vitro, and in view of this "in vivo" application is shown in sheet 1/1.

Figure 11:
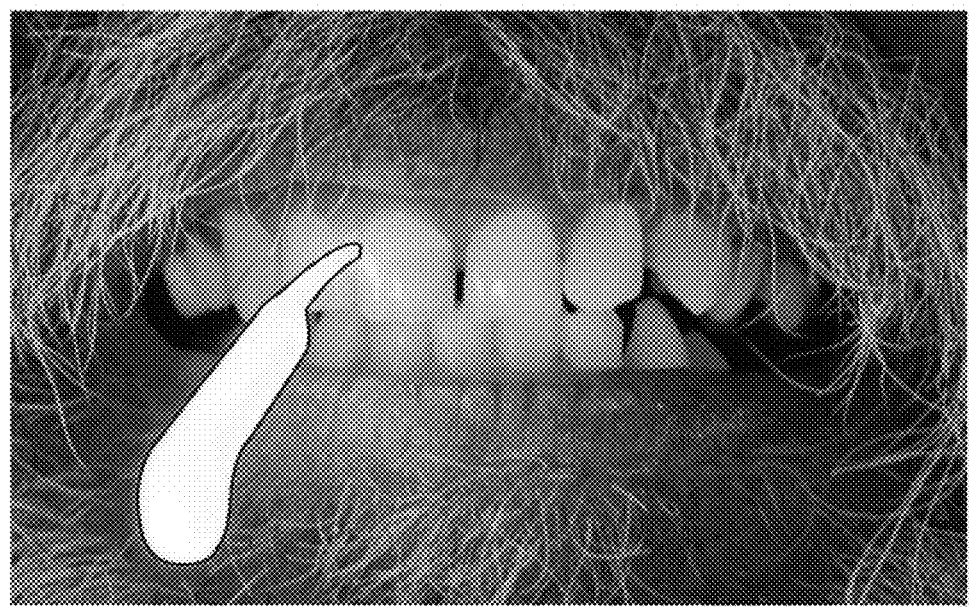

FIG. 11—Toothpick probe containing antiseptic/antibacterial shown in use in vivo (human mouth).

Description of antiseptic solutions used in above described protocol: Mint mouthwash—EQUATE® antiseptic blue mint mouth rinse containing as active ingredients: Eucalyptol 0.092%; Menthol 0.042%; Methyl salicylate 0.060%; and Thymol 0.064%. Inactive ingredients are: Water, alcohol 21.6%, sorbitol solution, flavor, poloxamer 407, benzoic acid, sodium saccharin, sodium benzoate, and FD&C green no. 3. The Citrus orange color mouth wash—EQUATE® antiseptic citrus mouth rinse has the same active ingredients as the above described Mint mouthwash. The inactive ingredients of this Citrus mouthwash are: water, alcohol 21.6%, sorbitol solution, flavor, poloxamer 407, benzoic acid, sucralose and/or sodium saccharin, sodium benzoate, cochineal extract.

The toothpick of this invention is called RXPIX for identification purposes in the protocol and is synonymous with toothpick probe molded or formed of nylon 6 material, readily absorbs moisture up to 8% of its weight and it is this moisture uptake by nylon 6 material that is the gist of this invention.

To mold nylon 6 material into a toothpick probe requires heating of nylon 6 to a plastic state then injecting into a cool mold cavity, and the toothpick moldings of the nylon 6 are immediately captured, on ejection from the molding cavities, and protected from absorption of moisture and water. After capture of the nylon 6 toothpick probe moldings from the molding cavities and protected from moisture absorption, the toothpicks of the nylon 6 material are immersed in a polar liquid antiseptic/antibacterial at which time the antiseptic/antibacterial permeates the toothpicks, after which the toothpicks, immersed in the antiseptic are dried and ready for subsequent use as a antiseptic/antibacterial toothpick probe in the human mouth in vivo, between the teeth or on the gums.

In all of the above protocol results described on page 5 (supra) and pictures shown in FIGS. 1-10, turbidity shows bacterial growth, and clarity shows no bacterial growth. The FIGS. show the efficacy of the procedure and protocol described, including molded nylon 6 absorption of a polar antiseptic/antibacterial solution, and subsequently leachable from the nylon 6 material in a liquid media, or as used in vivo, in the human mouth as a toothpick probe.

In addition to the toothpick probe, other applications for this process would include tooth prosthesis sections, molded of nylon 6 material, and immersed in a polar solution of antiseptic/antibacterial to absorb the antiseptic/antibacterial material and the prosthesis sections, placed in vivo, in the human mouth for leaching of the antiseptic/antibacterial to thwart initial bacterial growth on placement of the prosthesis section in vivo.

Other applications could be prosthesis, in vivo, of body parts molded of nylon 6 material and subsequent immersion of the molded parts in a polar solution of antiseptic/antibacterial components, then placing the molded parts containing the antiseptic/antibacterial in vivo position.

In the above examples the antiseptic/antibacterial components would be leached out of the nylon 6 section in a time interval after placement in vivo.

Having described my invention I claim:

1. A toothpick probe molding consisting of nylon-6 material and a polar antiseptic or antibacterial mouthwash solution, wherein said molding is captured and immediately immersed in said polar mouthwash solution for a time adequate to increase the weight of said toothpick by at least 10% after removing surface solution of said polar mouthwash solution from said molding.

2. A toothpick probe molding of claim 1, consisting of nylon-6 material and a polar solution of antiseptic or antibacterial mouthwash, wherein said polar solution is absorbed into said toothpick and wherein said toothpick is for probing between human teeth and gums.

* * * * *